United States Patent [19]
Renner et al.

[11] 3,978,087
[45] Aug. 31, 1976

[54] CYCLIC ACETALS CONTAINING EPOXIDE GROUPS

[75] Inventors: Alfred Renner, Munchenstein; Rolf Hügi, Basel, both of Switzerland

[73] Assignee: Ciba-Geigy Corporation, Ardsley, N.Y.

[22] Filed: Mar. 11, 1975

[21] Appl. No.: 557,449

Related U.S. Application Data

[62] Division of Ser. No. 332,840, Feb. 15, 1973, Pat. No. 3,884,944.

[30] Foreign Application Priority Data

Feb. 24, 1972 Switzerland.......................... 2638/73

[52] U.S. Cl. .............................................. 260/340.7
[51] Int. Cl.² ........................................ C07D 319/04

[58] Field of Search ................................. 260/340.7

[56] References Cited
UNITED STATES PATENTS

| | | | |
|---|---|---|---|
| 3,092,640 | 6/1963 | Mantell et al.................... | 260/340.7 |
| 3,136,785 | 6/1964 | Porret et al...................... | 260/340.7 |

*Primary Examiner*—Ethel G. Love
*Attorney, Agent, or Firm*—Vincent J. Cavalieri

[57] ABSTRACT

Cyclic acetals of 2-epoxy-propoxy-pivaldehydes. They can be used by themselves, if they contain two or more epoxy groups, or as reactive diluents in a mixture with other epoxide resins, and they give mouldings of excellent mechanical properties on curing with amines or acid anhydrides.

2 Claims, No Drawings

CYCLIC ACETALS CONTAINING EPOXIDE GROUPS

This is a divisional of application Ser. No. 332,840 filed on Feb. 15, 1973, now U.S. Pat. No. 3,884,944.

The subject of the invention are cyclic acetals containing epoxide groups, and their use in the manufacture of mouldings.

Diepoxides of the cyclic acetal from tetrahydrobenzaldehyde and cyclohex-2-ene-1,1-dimethylol are known from Swiss Patent specification No. 377,328. The mouldings manufactured therefrom display mechanical properties which leave something to be desired for certain end uses.

It has now been found that cyclic acetals containing epoxide groups, of the formula I given below, when used by themselves or, especially if they only contain one epoxide group in the molecule, when used as reactive diluents in a mixture with other epoxide resins, give mouldings of excellent mechanical properties on curing with amines or acid anhydrides.

The compounds according to the invention, which are easily accessible, are cycloacetals of 2-epoxypropoxypivaldehyde and correspond to the formula I

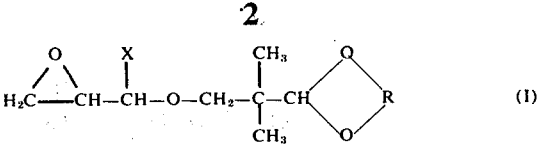

(I)

in which X denotes hydrogen or the methyl group and R denotes a divalent hydrocarbon radical or which the partial molecular weight is at most 500 and which can additionally contain ether oxygen atoms or oxygen atoms in hydroxyl, carbonyl or epoxide groups, but does not possess any other reactive groups.

Preferably, compounds of the formula I are concerned in which R denotes a group of the formula

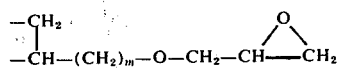

in which $m$ represents a number from 1 to 6, or in which R denotes a group of the formula

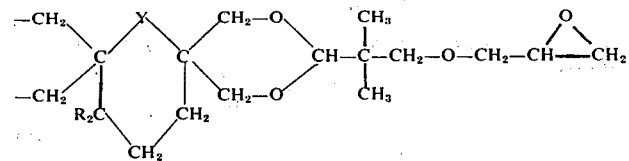

wherein Y represents

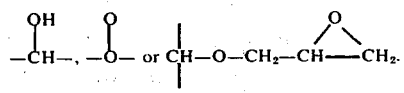

Typical examples of such cycloacetals of 2-epoxypropoxypivaldehyde are the following compounds:

(III)

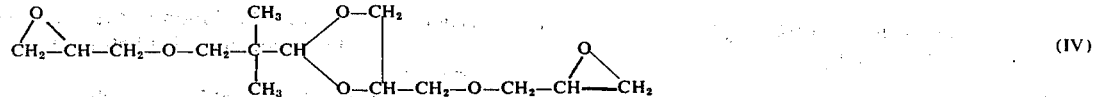

(IV)

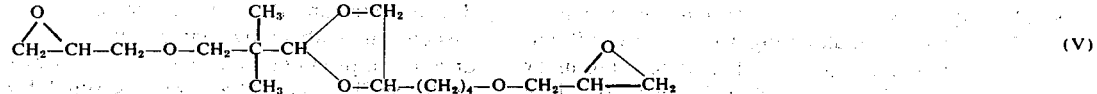

(V)

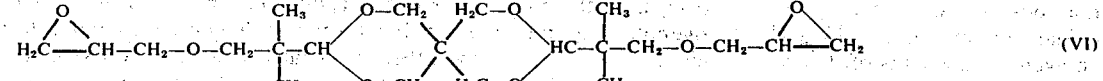

(VI)

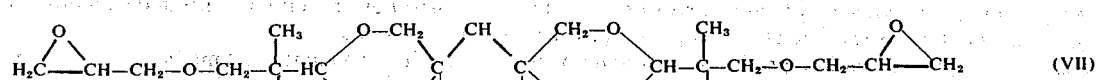

(VII)

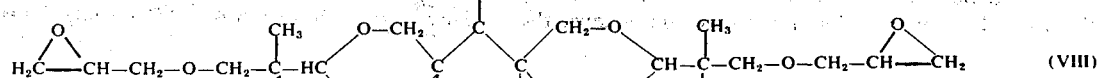

(VIII)

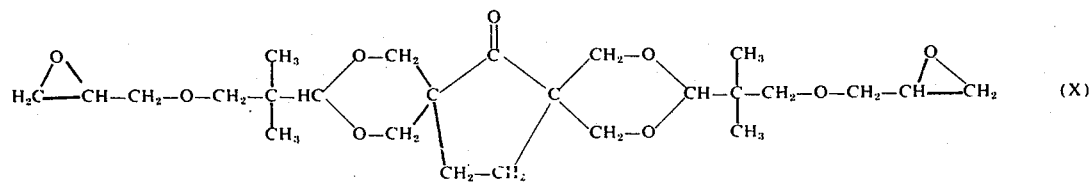

(X)

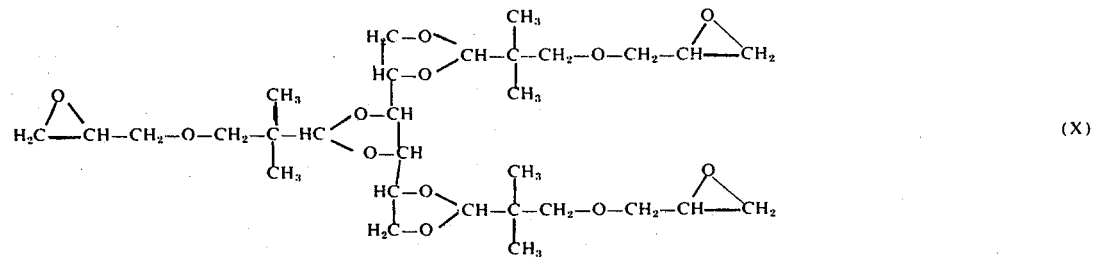

(X)

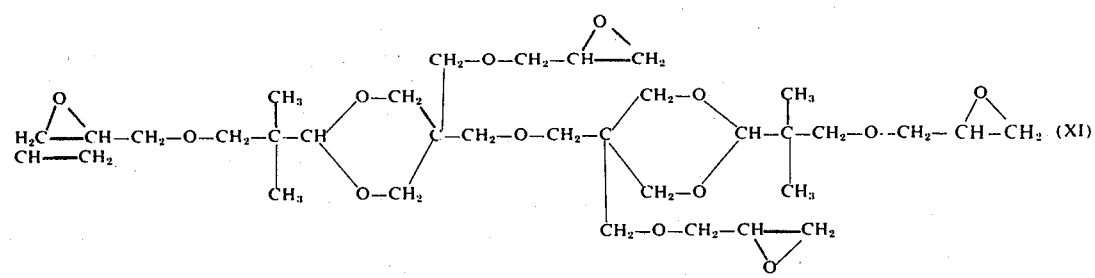

(XI)

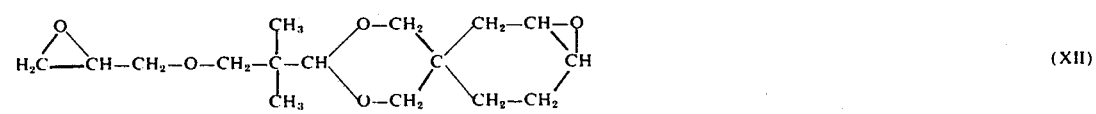

(XII)

According to the invention, the compounds of the formula I are manufactured by reacting a hydroxycycloacetal of the formula II

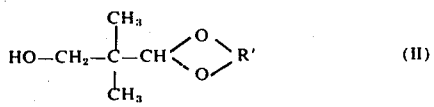

(II)

in which R' denotes a divalent hydrocarbon radical, of which the partial molecular weight is at most 500 and which can additionally contain ether oxygen atoms or oxygen atoms in hydroxyl or carbonyl groups, but does not possess any other reactive groups, with an epihalogenohydrin or β-methylepihalogenohydrin and an agent which splits off hydrogen halide.

The etherification of the hydroxycycloacetal with epichlorohydrin can be carried out according to 2 process variants, the choice of which depends on the solubility of the hydroxycycloacetal in epichlorohydrin. Readily soluble intermediate products are reacted with more than one mol of epichlorohydrin per hydroxy equivalent and with alkali hydroxide, optionally in the presence of a tetraalkylammonium halide catalyst, whilst removing water azeotropically. The alkali chloride formed in the etherification is removed by filtration or washed out and the excess epichlorohydrin is distilled off. Tetramethylammonium chloride or tetraethylammonium bromide in amounts of less than 1% can, for example, be used as the catalyst for the reaction. Instead of epichlorohydrin, epibromohydrin or methylepichlorohydrin can also be employed. In the latter case, the homologous methyl-glycidyl ethers are obtained. In a preferred embodiment, the water (water of reaction and water of solution of the alkali hydroxide) is removed by azeotropic distillation under reduced pressure.

Hydroxycycloacetals of low solubility in epichlorohydrin are appropriately reacted in dioxane solution or suspension, with equivalent amounts of epichlorohydrin in the presence of a Lewis acid (for example BF$_3$, SnCl$_4$, SbCl$_5$ and the like), as is described, for example, in DOS No. 1,956,490. The 2-hydroxy-3-chloropropyl-ether thus formed is dehydrohalogenated to the glycidyl ether by means of alkali hydroxide in a second process stage. This dehydrohalogenation can be carried out in the presence or in the absence of solvents; alkali hydroxides or their concentrated aqueous solutions can be employed.

In the first-mentioned method, by-products of higher molecular weight are formed; the residual chlorine content of the products of the process is generally very low ( 1%). The second method gives a smaller proportion of higher-molecular by-products and hence the viscosity of the resins manufactured in this way is lower. Since the addition of epichlorohydrin to the 2-hydroxy-3-chloropropyl-ether group according to:

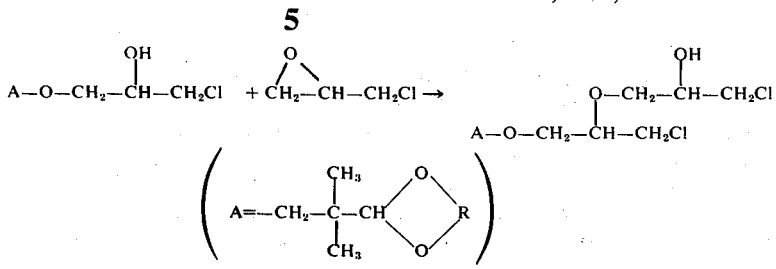

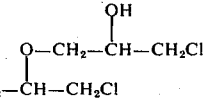

cannot be completely suppressed in the presence of Lewis acids, chlorohydrin ethers are formed, the chlorine atoms of which cannot be eliminated with solid or aqueous alkali under the conditions of the dehydrohalogenation. Hence, the resins manufactured according to the second method in general contain 1–3% of non-hydrolysable chlorine.

The starting products of the formula II can be manufactured by reacting 1 mol of the dimeric hydroxypivaldehyde, which according to Spath and v. Szilagyi (Berichte der deutschen chemischen Gesellschaft 76 B, page 949–956, 1943) is in the form of a cyclic semi-acetal of the following formula:

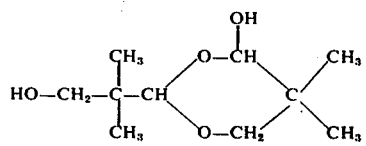

in the presence of a strong acid, preferably in aqueous solution containing hydrochloric acid, at temperatures below 20°C, with 2 mols of an at least dihydric alcohol of the formula
R'(OH)$_2$
with 2 mols of the hydroxycycloacetal of the formula II being obtained whilst 2 mols of water are split off.

The dimeric hydroxypivaldehyde is a crystalline compound of melting point = 90°–95°C. Examples of polyhydric alcohols which are suitable for the cycloacetalisation: ethylene glycol, 1,2- and 1,3-propylene glycol, 1,2- and 1,3-butylene glycol, cis-1,4-butenediol, glycerine, trimethylolpropane, 1,2,6-hexanetriol, pentaerythritol, dipentaerythritol, mannitol, sorbitol, 2,6-tetrahydroxymethyl-cyclohexanol or -cyclohexanone, 2,5-tetrahydroxymethylcyclopentanone and Δ3-cyclohexenedimethanol-1.

Depending on the structure and molecular weight, the products according to the invention are either liquid resins of low to medium viscosity or crystalline or resinous solids of pale colour and good stability to light. Since they also display good solubility in organic solvents they are particularly suitable for use as lacquer raw materials and as impregnating and dipping resins. The solid cycloacetals of 2-epoxypropoxypivaldehyde are particularly suitable for use as components of compression moulding compositions, laminating resins and fluidised bed powders. Surprisingly, certain individual compounds, for example the products according to the formulae IV and V, gave mouldings of high elongation at break and high tensile strength after curing with anhydride or amine. They are therefore suitable for use as plasticisers for other epoxide resin systems, whilst the products of lowest viscosity (for example III) can be used as reactive diluents.

Suitable curing agents for the cyclic acetals from 2-epoxypropoxypivaldehyde are above all polycarboxylic acid anhydrides such as phthalic anhydride, tetrahydrophthalic anhydride and hexahydrophthalic anhydride, pyromellitic dianhydride and various others, and also polycarboxylic acids, polymercaptans and polyamines, such as diethylenetriamine, triethylenetetramine, dimethylaminopropylamine, m-phenylenediamine and 4,4'-diaminodiphenylmethane. It is also possible to use polymerisation catalysts for the epoxide group, such as boron fluoride and its complexes with ethers, alcohols, phenols, carboxylic acids and amines, as curing agents. Furthermore, the fillers, pigments, fibres, plasticisers, accelerators and dyestuffs customary in the technology of the epoxide resins can be added to the curable mixtures.

The curable mixtures can also contain other epoxide resins, above all those based on bisphenol A, in any desired proportions.

The manufacture of the starting compounds of the formula II is described below for individual compounds (compounds A to J):

Compound A

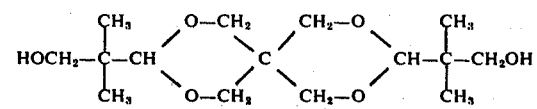

136 g (1 mol) of pentaerythritol are dissolved in 1 liter of concentrated hydrochloric acid in a sulphonation flask with stirrer and gas outlet tube. 204 g (1 mol) of dimeric β-hydroxy-pivaldehyde are added in portions whilst cooling to 15 – 20°C. The mixture is stirred for 24 hours at room temperature and is subsequently diluted with 1 liter of water whilst cooling. The reaction product is filtered off, washed with water until free of acid and dried in a vacuum drying cabinet at 100°C. The crude yield is 248 g (81%). The crude product is recrystallised from 2 liters of ethanol. 210 g (69%) of purified product of melting point 198°C are obtained.

Analysis for C$_{15}$H$_{28}$O$_6$ (304.37): calculated C 59.19; H 9.37;
Found: C 59.23; H 9.28.

Compound B

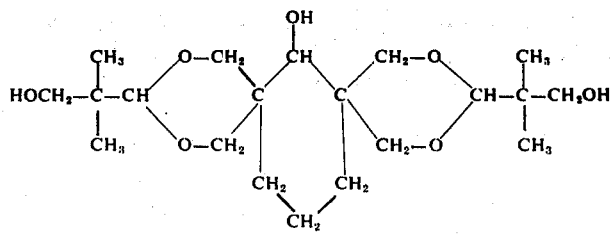

55 g (0.25 mol) of 2,2,6,6-tetramethylol-cyclohexanol are taken up in 500 ml of 12% strength hydrochloric acid in a sulphonation flask with stirrer and gas outlet tube. 51 g (0.25 mol) of dimeric β-hydroxypivaldehyde are added in portions whilst cooling to 15°–20°C. The reaction mixture is stirred for 24 hours at room temperature. Thereafter, the white crystalline precipitate is filtered off and the filter residue is washed with water until free of acid and dried in a vacuum drying cabinet at 100°C. 74 g (76% of theory) of the crude product are obtained. This is recrystallised from 185 ml of water and 370 ml of ethanol. 64 g (66%) of purified product of melting point 185°–190°C are obtained.

Analysis for $C_{20}H_{36}O_7$ (388.49): calculated: C 61.83; H 9.34;
found: C 61.72; H 9.35.

chloric acid in a sulphonation flask with stirrer and gas outlet tube. 51 g (0.25 mol) of finely powdered dimeric β-hydroxypivaldehyde are added in portions whilst cooling to 15°–20°C. The reaction mixture is stirred for 1 hour at room temperature and is then diluted with 100 ml of water, after which it is stirred for a further 5 hours. For working up, the mixture is diluted with 0.5 liter of water and the product is filtered off, washed until free of acid and dried in vacuo at 60°C. Crude yield 63 g (68% of theory) of white product. This is recrystallised from about 800 ml of ethanol and 55 g (60%) of pure product of melting point 230°–233°C are obtained.

Analysis for $C_{19}H_{32}O_7$ (372.45): calculated: C 61.27; H 8.66;
found: C 61.52; H 8.58, molecular weight: 371.

Compound C

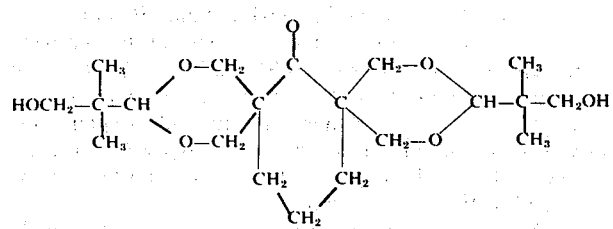

218 g (1 mol) of 2,2,6,6-tetramethylol-cyclohexanone are taken up in 1,250 ml of concentrated hydrochloric acid in a sulphonation flask with stirrer and gas outlet tube. 204 g (1 mol) of dimeric β-hydroxypivaldehyde are added in portions whilst cooling to 15°–20°C. The reaction mixture is stirred for 24 hours at room temperature. Thereafter 500 ml of water are added dropwise whilst cooling and the mixture is stirred for a further 12 hours at room temperature. It is finally diluted with 2.5 liters of water and the product which has precipitated is centrifuged off, washed until free of acid and dried in vacuo at 80°C. Crude yield 236 g (61% of theory). The crude yield is recrystallised from approx. 5 liters of ethanol. 193 g (50%) of pure product of melting point 228°–226° are obtained.

Analysis for $C_{20}H_{34}O_7$ (386.47). calculated: C 62.15; H 8.87;
found: C 62.31; H 8.80.

Compound E

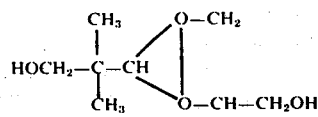

184 g (2 mols) of anhydrous glycerine, 204 g (1 mol) of dimeric β-hydroxypivaldehyde, 4 ml of concentrated sulphuric acid and 1,600 ml of toluene are initially introduced into a sulphonation flask with a simple water separator. The mixture is slowly heated to refluxing. After the theoretical amount of water (36 ml) has been separated off, which is the case after about 3 hours, the mixture is allowed to cool and is neutralised with 50 g of 10% strength aqueous sodium carbonate solution. Thereafter the toluene and water are stripped off in vacuo, the residue is taken up in methanol and the salt is filtered off. After removing the methanol in Compound D

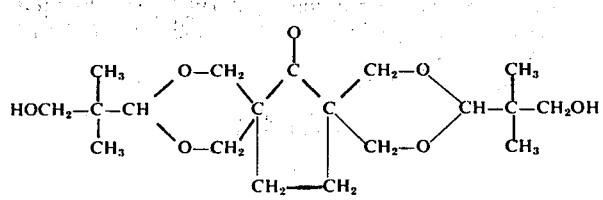

51 g (0.25 mol) of 2,2,5,5-tetramethylol-cyclopentanone are taken up in 300 ml of concentrated hydrovacuo, 350 g (99%) of crude product are obtained in the form of a yellow oil. Distillation yields 286 g (81%)

of the main fraction of boiling range 112°–115°C at 0.01 mm Hg.

Analysis for $C_8H_{16}O_4$ (176.21): calculated: C 54.51; H 9.16;
found: C 54.8; H 9.2. Molecular weight: 184.

According to a gas chromatogram, the product is an isomer mixture with

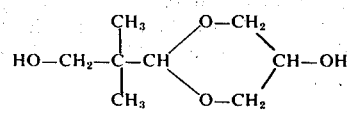

Compound F

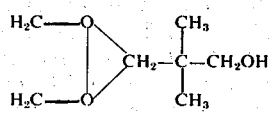

248 g (4 mols) of anhydrous ethylene glycol. 408 g (2 mols) of dimeric β-hydroxypivaldehyde. 8 ml of sulphuric acid and 2,400 ml of toluene are initially introduced into a sulphonation flask with a simple water separator. The mixture is slowly heated to refluxing. After 4 mols of water have been separated off, which is the case after about 6 hours, the mixture is cooled and neutralised with 100 g of 10% strength sodium carbonate solution. The water phase is separated off in a separating funnel, the toluene phase is dried with sodium sulphate and the toluene is stripped off in vacuo at 50°C. Crude yield: 489 g (84%) of a light yellow oil. The crude product is purified by distillation. The main fraction passes over at 108°–110°C at 25 mm Hg, yields 346 g (59.3%) of purified product and, according to a gas chromatogram, is about 95–98% pure.

Analysis for $C_7H_{13}O_3$ (146.18) calculated: C 57.51; H 9.68;
found: C 57.77; H 9.66.

Compound G

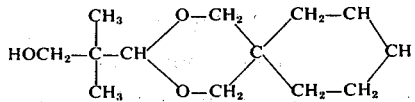

142 g (1 mol) of dimethylol-cyclohexene-3, 102 g (0.5 mol) of dimeric β-hydroxypivaldehyde, 2 ml or concentrated sulphuric acid and 800 ml of toluene are initially introduced into a sulphonation flask with a simple water separator. The mixture is slowly heated to refluxing. After 1 mol of water has been separated off, which is the case after about 8 hours, the mixture is cooled and is neutralised with 40 ml of 20% strength sodium carbonate solution. The aqueous phase is separated off in a separating funnel. The toluene phase is dried with sodium sulphate and concentrated in vacuo. Crude yield: 224 g (99% of theory) of a light oil. The crude product is distilled through a Vigreux column, whereupon the main fraction passes over at 114°–116°C at 0.14 mm Hg. 162 g (72%) of the distilled product are obtained:

Analysis for: $C_{13}H_{22}O_3$ calculated: C 68.99; H 9.80;
found: C 68.49; H 9.78.

Compound H

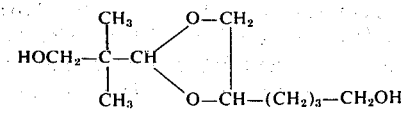

402 g (3 mols) of distilled 1,2,6-hexxanetriol, 306 g (1.5 mols) of dimeric β-hydroxypivaldehyde, 6 ml of concentrated sulphuric acid and 2.4 liters of toluene are initially introduced into a sulphonation flask with a simple water separator. The mixture is slowly heated to refluxing. After 3 mols of water have been separated off, which is the case after about 6 hours, the mixture is cooled and is neutralised with 100 g of 10% strength sodium carbonate solution. The two-phase batch is filtered and the filtrate is concentrated in vacuo. The residue, containing salt, is taken up in methanol, the salt is filtered off and the methanol is stripped off in vacuo. Crude yield: 653 g (100% of theory) of a yellow oil. The crude product is purified by distillation through a Vigreux column. After first runnings of 104 g, the main fraction passes over at 124°–126°C at 0.07 mm Hg.

Yield: 410 g (63%) of a clear, light oil.
Analysis for: $C_{11}H_{22}O_4$ (218.29) calculated: C 60.52; H 10.16;
found: C 60.10; H 10.20.

Compound J

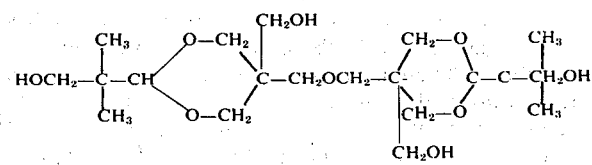

63.5 g (0.25 mol) of dipentaerythritol, 51 g (0.5 mol) of dimeric β-hydroxypivaldehyde, 1 ml of concentrated sulphuric acid and 300 ml of toluene are initially introduced into a sulphonation flask with a simple water separator. The mixture is slowly heated to refluxing. After 9 ml of water have been separated off, which is the case after about 6 hours, the mixture is cooled and is neutralised with 20 g of 10% strength sodium carbonate solution. After separating off the aqueous phase and drying with sodium sulphate, the mixture is completely concentrated. 104 g (98% of theory) of a resinous residue are obtained; this is dissolved in 100 ml of chloroform and the solution is left to stand in the cold for some time. The crystals which have precipitated are filtered off and dried in vacuo at 50°C. Yield: 42 g (40% of theory) of white crystals of melting point 130°C.

Analysis calculated for $C_{20}H_{38}O_9$ (422.50):
Calculated: C 56.85; H 9.07;
Found: C 56.09; H 8.89.

EXAMPLE 1

Compare formula VI 173 g (0.569 mol) of the diol A, 600 ml of anhydrous dioxane and 2.5 g of $SnCl_4$ are initially introduced into a sulphonation flask with reflux condenser, thermometer and dropping funnel. The mixture is heated to 100°C and 105.5 g (1.138 mol) of epichlorohydrin are thereafter added dropwise over the course of 3 hours. After half the period of dropwise addition, a further 0.8 g of SnCl₄ is added. After all the epichlorohydrin has been added dropwise, the epoxide content should be less than 0.02 equivalent/kg. Thereafter, the dioxane is rapidly stripped off at 100°C and 20 mm Hg, the residue is allowed to cool and 960 g of toluene are added. The mixture is heated to 50°C, a Hefel separator is fitted and 109.5 g of 50% strength sodium hydroxide solution are added dropwise over the course of two hours whilst azeotropically removing the water in a partial vacuum. The reaction is allowed to continue until the theoretical amount of water has separated off. The mixture is then allowed to cool and 960 g of water are added to dissolve the salt formed. The organic phase is separated off in a separating funnel, washed with 48 g of 10% strength sodium dihydrogen phosphate solution and finally dried with sodium sulphate. The toluene is stripped off on a rotary evaporator at maximally 100°C.

Yield: 235 g (99% of theory), epoxide content: 3.95 equivalents/kg (82% of theory); $Cl_{total}$: 2.40.

EXAMPLE 2

Compare formula VII 186.5 g (0.48 mol) of the diol B, 1.5 l of anhydrous dioxane and 4 g of SnCl₄ are initially introduced into a sulphonation flask with reflux condenser, thermometer and dropping funnel. The mixture is heated to 100°C and 89.0 g (0.96 mol) of epichlorohydrin are subsequently added dropwise over the course of three hours. After half the period of the dropwise addition, a further 1 g of SnCl₄ is added. When all the epichlorohydrin has been added dropwise, the epoxide content should be less than 0.03 equivalent/kg. Thereafter the dioxane is rapidly distilled off at 100°C and 15–20 mm Hg and the residue is allowed to cool and taken up in 2 liters of toluene. The solution is heated to 50°C, a Hefel separator is fitted and 92 g (1.15 mol) of 50% strength sodium hydroxide solution are added dropwise over the course of two hours whilst azeotropically removing the water in a partial vacuum. The reaction is allowed to continue until the theoretical amount of water has separated off. The mixture is then allowed to cool and 2 liters of water are added to dissolve the salt formed. The organic phase is separated off in a separating funnel, washed with 80 g of 10% strength sodium dihydrogen phosphate solution and dried with sodium sulphate. The toluene is stripped off in vacuo at maximally 100°C.

Yield: 228 g (95% of theory), epoxide content: 2.50 equivalents/kg (62%); $Cl_{total}$: 1.3%.

EXAMPLE 3

Compare formula VIII 64 g (0.165 mol) of the diol C, 500 g of anhydrous dioxane and 1.2 g of SnCl₄ are initially introduced into a sulphonation flask with reflux condenser, thermometer, dropping funnel and stirrer. The mixture is heated to 100°C and 30.5 g (0.33 mol) of epichlorohydrin are added dropwise over the course of about three hours. After half the period of the dropwise addition, a further 0.5 g of SnCl₄ is added. After completion of the addition reaction, the epoxide content of the reaction mixture should be less than 0.02 equivalent/kg. Thereafter the dioxane is rapidly stripped off at 190°C and 20–25 mm Hg, the residue is allowed to cool and the chlorohydrin ether is taken up in 600 g of toluene. The solution is heated to 50°–55°C, a Hefel separator is fitted and 31.7 g (0.396 mol) of 50% strength sodium hydroxide solution are added dropwise over the course of two hours whilst azeotropically removing the water in a partial vacuum. The reaction is allowed to continue until the theoretical amount of water has separated off. After cooling, 600 g of water are added to dissolve the salt formed. The organic phase is separated off in a separating funnel, washed with 25 g of 10% strength sodium dihydrogen phosphate solution until neutral and then dried with sodium sulphate. The toluene is stripped off in vacuo at maximally 100°C.

Yield: 81.0 g (98% of theory) of a highly viscous resin of epoxide content 2.77 equivalents/kg (69% of theory).

EXAMPLE 4

Compare formula IX 178.5 g (0.48 mol) of the diol D, 500 g of anhydrous dioxane and 2.2 g of SnCl₄ are initially introduced into a sulphonation flask with reflux condenser, thermometer, dropping funnel and stirrer. The mixture is heated to 100°C and 89 g (0.96 mol) of epichlorohydrin are added dropwise over the course of about three hours. When half the epichlorohydrin has been added dropwise, a further 0.7 g of SnCl₄ is added. After completion of the addition of epichlorohydrin, the epoxide content in the reaction mixture should be less than 0.02 equivalent/kg. Thereafter the dioxane is rapidly stripped off at 100°C and 20 mm Hg and the residue is allowed to cool and is taken up in 820 g of toluene. The mixture is heated to 55°C, a Hefel separator is fitted and 92 g (1.15 mols) of 50% strength sodium hydroxide solution are added dropwise over the course of about two hours whilst azeotropically removing the water in a partial vacuum. The reaction is allowed to continue until the theoretical amount of water has separated off. After cooling, 820 g of water are added to dissolve the salt formed. The organic phase is separated off in a separating funnel, washed with 40 g of 10% strength sodium dihydrogen phosphate solution until neutral and dried with sodium sulphate. The toluene is stripped off in vacuo at maximally 100°C. Yield: 229 g (98.5%). The solid resin has an epoxide content of 3.16 equivalents/kg (76.5%). $Cl_{total}$: 1.5%.

EXAMPLE 5

Compare formula III 332 g (2.28 mols) of the acetal E. 1.055 g (11.4 mols) of epichlorohydrin and 11.4 g of 50% strength aqueous tetramethylammonium chloride solution are initially introduced into a sulphonation flask with a Hefel separator, thermometer and dropping funnel. The mixture is heated to 52°–54°C and 201 g (2.51 mols) of 50% strength sodium hydroxide solution are added dropwise at this temperature over the course of about two hours, whilst simultaneously removing the water azeotropically at 70–75 mm Hg. After complete addition of the sodium hydroxide solution, the mixture is allowed to continue reacting until the theoretical amount of water has separated off. The mixture is allowed to cool and 500 g of water are added to dissolve the salt formed. The organic phase is separated off in a separating funnel, washed with 80 g of 5% strength sodium dihydrogen phosphate solution until neutral and dried with sodium sulphate. The excess epichlorohydrin is stripped off completely in vacuo at 80°. Yield: 390 g (85%) of a light yellow liquid of epoxide content 4.06 equivalents/kg (82%).

EXAMPLE 6 a) 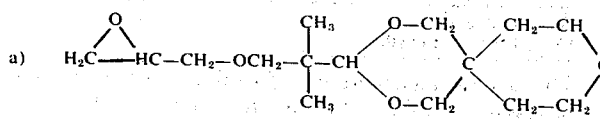

(XII')

678 g (3 mols) of the acetal G, 1,390 g (15 mols) of epichlorohydrin and 15 g of 50% strength aqueous tetramethylammonium chloride solution are initially introduced into a sulphonation flask with a Hefel separator, thermometer and dropping funnel. The mixture is heated to 54°–56°C and 264 g (3.3 mols) of 50% strength sodium hydroxide solution are added dropwise at this temperature over the course of about two hours, whilst simultaneously removing the water azeotropically at 70–75 mm Hg. After complete addition of the sodium hydroxide solution the mixture is allowed to continue reacting until the theoretical amount of water has separated off. The mixture is allowed to cool and 700 g of water are added to dissolve the salt formed. The organic phase is separated off in a separating funnel, washed with 100 g of 5% strength aqueous sodium dihydrogen phosphate solution until neutral and dried with sodium sulphate. The excess epichlorohydrin is stripped off completely in vacuo at 80°C. Yield: 800 g (94.6%) of a light yellow liquid of epoxide content 2.64 (74.5%).

b. Compare formula XII 960 g (3.4 mols) of the resulting monoglycidyl ether (XII') and 2,900 g of ethyl acetate are initially introduced into a sulphonation flask with reflux condenser. This mixture is heated to 50°C and the dropwise addition of 467 g (3.74 mols) of 61% strength aqueous peracetic acid is started. At the same time 15% strength sodium carbonate solution is added dropwise, controlled by pH measurement using a Titrator in such a way that the pH value of the reaction mixture always remains between 5.4 and 5.6. The reaction is slightly exothermic. After 80 minutes the dropwise addition of the peracetic acid is complete and up to this point in time 200 ml of sodium carbonate solution have been consumed. After a further 4½ hours' post-reaction at 50°C, the conversion of peracetic acid has risen to over 95% and the consumption of sodium carbonate solution has risen to 510 ml. The batch is cooled and adjusted to pH 11 with 150 ml of 50% strength aqueous sodium hydroxide solution at room temperature. The batch is subsequently separated in a separating funnel, neutralised with 650 ml of 15% strength $NaH_2PO_4$ solution, washed twice with 500 ml of water at the time, dried over sodium sulphate and concentrated at 60°C, and the residue is finally dried for 1 hour at 90°C and 14 mm Hg.

Yield: 964 g of a light yellow liquid (95% of theory) having an epoxide content of 5.40 equivalents/kg (80.3% of theory).

EXAMPLE 7

Compare formula V 371 g (1.7 mols) of the diol H, 1,570 g of epichlorohydrin and 17 g of 50% strength aqueous tetramethylammonium chloride solution are initially introduced into a sulphonation flask with a Hefel separator, thermometer and dropping funnel. The mixture is heated to 52–54°C and 300 g (3.75 mols) of 50% strength sodium hydroxide solution are added dropwise at this temperature over the course of about 2 hours whilst simultaneously removing the water azeotropically at 70–75 mm Hg. After completion of the addition of sodium hydroxide solution, the mixture is allowed to continue reacting until the theoretical amount of water has separated off. The mixture is allowed to cool and 650 g of water are added to dissolve out the salt formed. The organic phase is separated off in a separating funnel, washed with 100 g of aqueous 5% strength sodium dihydrogen phosphate solution until neutral and dried with sodium sulphate. The epichlorohydrin is stripped off in vacuo at 80°C. Yield: 522 g (93.4%) of liquid resin of epoxide content 5.42 equivalents/kg (89.5%).

EXAMPLE 8

Compare formula IV 362 g (2.06 mols) of the acetal of the formula E

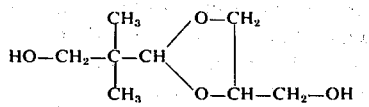

1,910 g (20.6 mols) of epichlorohydrin and 20.6 g of 50% strength aqueous tetramethylammonium chloride solution are initially introduced into a sulphonation flask with a Hefel separator, thermometer and dropping funnel. The mixture is heated to 52°–54°C and at this temperature 364 g (4.54 mols) of 50% strength sodium hydroxide solution are added dropwise over the course of about 2 hours, whilst simultaneously removing the water azeotropically at 70–80 mm Hg. After completion of the addition of the sodium hydroxide solution, the mixture is allowed to continue reacting until the theoretical amount of water has separated off. The mixture is allowed to cool and 800 g of water are added to dissolve the salt formed. The organic phase is separated off in a separating funnel, washed with 120 g of aqueous 5% strength sodium dihydrogen phosphate solution until neutral and dried with sodium sulphate. The excess epichlorohydrin is stripped off in vacuo at 80°C. Yield: 450 g (76%) of yellow liquid resin of epoxide content 6.09 equivalents/kg (88%).

EXAMPLE 9

Compare formula XI 105.5 g (0.25 mol) of the polyol J, 925 g (10 mols) of epichlorohydrin and 10 g of 50% strength aqueous tetramethylammonium chloride solution are initially introduced into a sulphonation flask with a Hefel separator, thermometer and dropping funnel. The mixture is heated to 52°–54°C and 92 g (1.15 mols) of 50% strength aqueous sodium hydroxide solution are added dropwise at this temperature over the course of about one hour, whilst simultaneously azeotropically removing the water from the sodium hydroxide solution, and the water of reaction, at 70–80 mm Hg. After completion of the addition of the sodium hydroxide solution, the mixture is allowed to continue to react until the theoretical amount of water has separated off. The mixture is allowed to cool and 250 ml of water are added to dissolve out the salt formed. The organic phase is separated off in a separating funnel, neutralised with 100 g of 10% strength aqueous $NaH_2PO_4$ solution, washed with 250 ml of water and dried over sodium sulphate. The excess epichlorohydrin is stripped off in vacuo at 80°C. Yield: 147.5 g of yellow, clear resin (91% of theory) of epoxide content 4.93 equivalents/kg (80% of theory); $Cl_{total}$ 1.225%.

Examples of Applications

Table 1 which follows gives the conditions under which some of the cyclic acetals, containing epoxide groups, which have been described are cured, and the properties of the cured mouldings. In this table the symbols denote the following:

| | |  | |
|---|---|---|---|
| A | Hexahydrophthalic anhydride | | |
| B | Isophoronediamine | | |
| C | Methylnadic anhydride | | |
| HD | Heat distortion | ISO/R 75 | °C |
| WA | Water absorption | 4 days/20°C | % |
| IS | Impact strength | VSM 77.105 | kpcm/cm² |
| TS | Tensile strength | VSM 77.101 | kp/mm² |
| EB | Elongation at break | VSM 77.101 | % |
| DF | Deflection | VSM 77.103 | mm |
| FS | Flexural strength | VSM 77.103 | kp/mm² |

The glycidyl ethers are mixed with the curing agents, if necessary at 60° to 80°C, and the mixture is deaerated in a high vacuum and thereafter cast to give slabs of size 200 × 400 × 4 mm.

| Example No. | Glycidyl ether No. | Parts of glycidyl ether | Parts of curing agent | Curing conditions | HD | WA | IS | TS | EB | DF | FS |
|---|---|---|---|---|---|---|---|---|---|---|---|
| 1 | IV | 70 | 39.2 A | 5hrs. 120°C/24 hrs.140°C | 33 | 0.54 | 43.2 | 2.3 | 80 | 20 | 4.6* |
| 2 | IV | 100 | 18.2 B | 2hrs. 40°C/ 1 hr.150°C | 34 | 0.56 | 73.1 | — | — | 20 | 5.3* |
| 3 | VI | 70 | 34.4 A | 5hrs.120°C/24hrs.140°C | 63 | 0.18 | 18.3 | 6.7 | 4.4 | 6.1 | 12.6 |
| 4 | VI | 100 | 15.9 B | 2hrs. 80°C/ 1 hr.150°C | 74 | 0.29 | 21.1 | 5.2 | 3.8 | 11.5 | 13.1 |
| 5 | VII | 68 | 30.6 C | 5hrs.120°C/24hrs.140°C | 103 | 0.32 | 19.6 | 2.3 | — | — | 11.0 |
| 6 | VIII | 78 | 28.3 A | 5hrs.120°C/24hrs.140°C | 59 | 0.21 | 1.1 | 1.9 | 1.7 | 1.5 | 2.8 |
| 7 | IX | 76 | 31.5 A | 5hrs.120°C/24hrs.140°C | 66 | 0.23 | 26.0 | 6.2 | 4.4 | 7.3 | 11.0 |
| 8 | VI | 118 | 76.2 A | 5hrs.120°C/24hrs.140°C | 66 | 0.29 | 17.1 | 6.9 | 4.3 | 10.8 | 10.4 |
| 9 | XII | 110 | 77.3 A | 5hrs. 80°C/24hrs.140°C | 94 | 0.32 | 12.7 | 7.7 | 3.7 | 6.6 | 9.3 |

*No fracture

We claim:
1. A cyclic acetal of 2-epoxy-propoxy-pivaldehyde of the formula

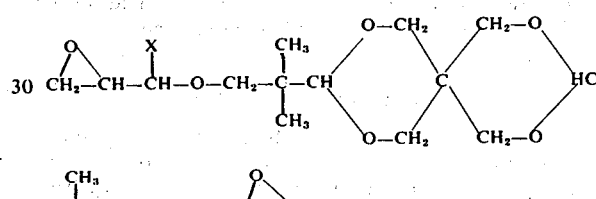

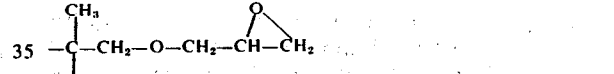

wherein X is hydrogen or methyl.

2. Acetal according to claim 1 of the formula

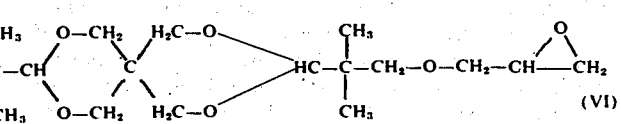

(VI)

* * * * *